(12) United States Patent
Janka et al.

(10) Patent No.: US 9,206,149 B2
(45) Date of Patent: *Dec. 8, 2015

(54) OXIDATION PROCESS TO PRODUCE A CRUDE DRY CARBOXYLIC ACID PRODUCT

(71) Applicant: EASTMAN CHEMICAL COMPANY, Kingsport, TN (US)

(72) Inventors: Mesfin Ejerssa Janka, Kingsport, TN (US); Kenny Randolph Parker, Afton, TN (US); Ashfaq Shahanawaz Shaikh, Kingsport, TN (US); Lee Reynolds Partin, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/282,360

(22) Filed: May 20, 2014

(65) Prior Publication Data

US 2014/0256964 A1    Sep. 11, 2014

Related U.S. Application Data

(63) Continuation of application No. 13/758,088, filed on Feb. 4, 2013, now Pat. No. 8,772,513.

(60) Provisional application No. 61/694,982, filed on Aug. 30, 2012.

(51) Int. Cl.
    C07D 307/34    (2006.01)
    C07D 307/68    (2006.01)
    C07D 307/48    (2006.01)

(52) U.S. Cl.
    CPC .......... *C07D 307/68* (2013.01); *C07D 307/48* (2013.01)

(58) Field of Classification Search
    CPC .................................................. C07D 307/34
    USPC .................................... 549/485; 562/485
    See application file for complete search history.

(56) References Cited

U.S. PATENT DOCUMENTS

| | | | |
|---|---|---|---|
| 2,797,197 A | 6/1957 | Thompson et al. | |
| 3,203,963 A | 8/1965 | Hales et al. | |
| 3,326,944 A | 6/1967 | Lew | |
| 4,977,283 A | 12/1990 | Leupold et al. | |
| 6,737,481 B1 | 5/2004 | Kurian et al. | |
| 7,052,764 B2 | 5/2006 | Chang et al. | |
| 7,385,081 B1 | 6/2008 | Gong | |
| 7,411,078 B2 | 8/2008 | Miura et al. | |
| 7,572,925 B2 | 8/2009 | Dumesic et al. | |
| 7,700,788 B2 | 4/2010 | Lilga et al. | |
| 8,183,020 B2 | 5/2012 | Hanke | |
| 8,193,381 B2 | 6/2012 | Lilga et al. | |
| 8,193,382 B2 | 6/2012 | Lilga et al. | |
| 8,748,479 B2 | 6/2014 | Shaikh et al. | |
| 8,772,513 B2 * | 7/2014 | Janka et al. | 549/485 |
| 8,791,277 B2 * | 7/2014 | Janka et al. | 549/485 |
| 8,791,278 B2 * | 7/2014 | Shaikh et al. | 549/485 |
| 8,796,477 B2 * | 8/2014 | Janka et al. | 549/485 |
| 8,809,556 B2 * | 8/2014 | Janka et al. | 549/485 |
| 8,846,960 B2 * | 9/2014 | Janka et al. | 549/485 |
| 8,916,719 B2 | 12/2014 | Shaikh et al. | |
| 8,916,720 B2 | 12/2014 | Shaikh et al. | |
| 8,969,404 B2 | 3/2015 | Janka et al. | |
| 2003/0055271 A1 | 3/2003 | Grushin et al. | |
| 2006/0205977 A1 | 9/2006 | Sumner, Jr. et al. | |
| 2007/0232815 A1 | 10/2007 | Miura et al. | |
| 2009/0124829 A1 | 5/2009 | Gong | |
| 2009/0131690 A1 | 5/2009 | Gruter et al. | |
| 2009/0156841 A1 | 6/2009 | Sanborn et al. | |
| 2009/0326262 A1 | 12/2009 | Wan | |
| 2010/0210867 A1 | 8/2010 | Bustamante et al. | |
| 2011/0092720 A1 | 4/2011 | Yutaka et al. | |
| 2012/0302768 A1 | 11/2012 | Janka et al. | |

(Continued)

FOREIGN PATENT DOCUMENTS

| | | |
|---|---|---|
| CS | 87340 | 7/1959 |
| EP | 1 834 951 A1 | 9/2007 |

(Continued)

OTHER PUBLICATIONS

Notice of Allowance dated Apr. 1, 2014 received in co-pending U.S. Appl. No. 13/758,080.
Notice of Allowance dated Apr. 1, 2014 received in co-pending U.S. Appl. No. 13/758,070.
Office Action dated Apr. 17, 2014 received in co-pending U.S. Appl. No. 13/758,072.
Copending U.S. Appl. No. 14/259,754, filed Apr. 23, 2014, Ashfaq Shaikh et al.
Office Action dated Apr. 30, 2014 received in co-pending U.S. Appl. No. 13/798,235.

(Continued)

*Primary Examiner* — Golam M M Shameem
(74) *Attorney, Agent, or Firm* — Phan Law Group PLLC

(57) ABSTRACT

Disclosed is a process to produce a dry purified carboxylic acid product comprising furan-2,5-dicarboxylic acid (FDCA). The process comprises oxidizing at least one oxidizable compound selected from the following group: 5-(hydroxymethyl)furfural (5-HMF), 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feed-stocks of 5-HMF and 5-HMF esters and mixed feed-stocks of 5-HMF and 5-HMF ethers and mixed feed-stocks of 5-HMF and 5-alkyl furfurals to generate a crude carboxylic acid slurry comprising FDCA, cooling a crude carboxylic acid slurry in cooling zone to form a cooled slurry stream. The cooled slurry stream is routed to a solid-liquid separation zone to generate a crude wet cake stream comprising FDCA that is dried in a drying zone to generate a dry carboxylic acid product stream comprising crude FDCA (cFDCA).

10 Claims, 1 Drawing Sheet

(56) References Cited

U.S. PATENT DOCUMENTS

| | | |
|---|---|---|
| 2012/0302769 A1 | 11/2012 | Janka et al. |
| 2012/0302770 A1 | 11/2012 | Janka et al. |
| 2012/0302771 A1 | 11/2012 | Janka et al. |
| 2012/0302772 A1 | 11/2012 | Shaikh et al. |
| 2012/0302773 A1 | 11/2012 | Janka et al. |
| 2013/0345452 A1 | 12/2013 | Janka et al. |
| 2014/0024844 A1 | 1/2014 | Janka et al. |
| 2014/0142328 A1 | 5/2014 | Shaikh et al. |
| 2014/0235880 A1 | 8/2014 | Shaikh et al. |
| 2014/0364633 A1 | 12/2014 | Janka et al. |

FOREIGN PATENT DOCUMENTS

| | | |
|---|---|---|
| EP | 2 197 868 B1 | 4/2011 |
| EP | 2 197 865 B1 | 8/2012 |
| JP | 2007-261986 A | 10/2007 |
| JP | 2007-261990 A | 10/2007 |
| JP | 2009-001519 A | 1/2009 |
| JP | 2009-013079 A | 1/2009 |
| JP | 2009-242312 A | 10/2009 |
| SU | 162962 A | 9/1962 |
| WO | WO 02/098836 A1 | 12/2002 |
| WO | WO 2007/092183 A2 | 8/2007 |
| WO | WO 2008/054804 A2 | 5/2008 |
| WO | WO 2009/023174 A2 | 2/2009 |
| WO | WO 2009/030506 A4 | 3/2009 |
| WO | WO 2009/030507 A4 | 3/2009 |
| WO | WO 2010/077133 A1 | 7/2010 |
| WO | WO 2010/132740 A2 | 11/2010 |
| WO | WO 2011/043660 A2 | 4/2011 |
| WO | WO 2012/161968 A1 | 11/2012 |
| WO | 2014/193634 A1 | 12/2014 |
| WO | 2014/197195 A2 | 12/2014 |

OTHER PUBLICATIONS

Office Action dated Apr. 25, 2014 received in co-pending U.S. Appl. No. 13/228,797.
Office Action dated Apr. 25, 2014 received in co-pending U.S. Appl. No. 13/228,809.
Office Action dated Apr. 25, 2014 received in co-pending U.S. Appl. No. 13/798,257.
Notice of Allowance dated Apr. 28, 2014 received in co-pending U.S. Appl. No. 13/228,813.
Notice of Allowance dated Apr. 28, 2014 received in co-pending U.S. Appl. No. 13/228,803.
Notice of Allowance dated May 1, 2014 received in co-pending U.S. Appl. No. 13/228,799.
Office Action dated May 29, 2014 received in co-pending U.S. Appl. No. 13/228,816.
Notice of Allowance dated Jun. 11, 2014 received in co-pending U.S. Appl. No. 13/553,976.
Copending U.S. Appl. No. 14/309,010, filed Jun. 19, 2014, Janka et al.
Copending U.S. Appl. No. 14/317,588, filed Jun. 27, 2014, Parker et al.
Copending U.S. Appl. No. 14/317,692, filed Jun. 27, 2014, Janka et al.
Copending U.S. Appl. No. 14/317,782, filed Jun. 27, 2014, Parker et al.
Copending U.S. Appl. No. 14/317,875, filed Jun. 27, 2014, Janka et al.
Slavinskaya, V. A., et al., "Liquid-Phase Catalytic Oxidation of 5-Methylfurfural," React. Kinet. Catal. Lett., 1979, vol. 11, No. 3, pp. 215-220.
Gandini, A., et al., "Rapid Communication: The Furan Counterpart of Poly(ethylene terephthalate): An Alternative Material Based on Renewable Resources," Journal of Polymer Science: Part A: Polymer Chemistry, 2009, vol. 47, pp. 295-298, Wiley Periodicals, Inc.
Partenheimer, W. et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts," Adv. Synth. Catal., 2001, vol. 343, No. 1, pp. 102-111.
Lewkowski, J.; "Synthesis, Chemistry and Applications of 5-Hydroxymethylfurfural and its Derivatives," ARKIVOC, 2001, pp. 17-54.
Zakharov, I. V., "Mechanism of Initiation and Inhibition by Mn(II) in Hydrocarbon Oxidation in the Presence a Cobalt-Manganese Bromide Catalyst," Kinetics and Catalysis, 1998, vol. 39, No. 4, pp. 485-492.
Jiao, X. J. et al., "Kinetics of Manganese(III) Acetate in Acetic Acid: Generation of Mn(III) with Co(III), Ce(IV), and Dibromide Radicals; Reactions of Mn(III) with Mn(II), Co(II), Hydrogen Bromide, and Alkali Bromides," Inorg. Chem., 2000, vol. 39, pp. 1549-1554, American Chemical Society.
Copending U.S. Appl. No. 13/228,816, filed Sep. 9, 2011, Mesfin Ejerssa Janka, et al.
Copending U.S. Appl. No. 13/228,799, filed Sep. 9, 2011, Mesfin Ejerssa Janka, et al.
Copending U.S. Appl. No. 13/228,809, filed Sep. 9, 2011, Mesfin Ejerssa Janka, et al.
Copending U.S. Appl. No. 13/228,803, filed Sep. 9, 2011, Mesfin Ejerssa Janka, et al.
Copending U.S. Appl. No. 13/228,797, filed Sep. 9, 2011, Mesfin Ejerssa Janka, et al.
Copending U.S. Appl. No. 13/228,813, filed Sep. 9, 2011, Ashfaq Shaikh, et al.
PCT International Search Report and Written Opinion dated Jul. 27, 2012 for International Application No. PCT/US2012/037223.
PCT International Search Report and Written Opinion dated Aug. 7, 2012 for International Application No. PCT/US2012/037218.
PCT International Search Report and Written Opinion dated Jul. 27, 2012 for International Application No. PCT/US2012/037204.
PCT International Search Report and Written Opinion dated Aug. 3, 2012 for International Application No. PCT/US2012/037210.
Copending U.S. Appl. No. 13/553,976, filed Jul. 20, 2012, Mesfin Ejerssa Janka, et al.
PCT International Search Report and Written Opinion dated Aug. 23, 2012 for International Application No. PCT/US2012/037228.
Chheda et al., "Production of 5-hydromethylfurfural and furfural by dehydration of biomass-derived mono- and poly-saccharides." Green Chemistry, vol. 9, pp. 342-350 (2007).
Werpy et al., "Top Value Added Chemicals from Biomass" DOE (Pacific NW National Laboratory) (Aug. 2004).
Verevkin et al., "Biomass-Derived Platform Chemicals: Thermodynamic Studies on the Conversion of 5-Hydroxymethylfurfural into Bulk Intermediates" Ind. Eng. Chem. Res., vol. 48, pp. 10087-10093 (2009).
Manasek, Z., "Modification of a Fiber-Forming Polyester Based on 2,5-Furandicarboxylic Acid", Mar. 20, 1963, pp. 35-38, UDC 677.465.
Rodivilova et al., "Synthesis and Investigation of Polyarylates Based on 2,5-Furandicarboxylic Acid and Diphenylolpropane", Khimiya I Khimicheskaya Tekhnologiya, No. 7, 1968, pp. 818-821.
Copending U.S. Appl. No. 13/758,070, filed Feb. 4, 2013, Kenny Randolph Parker, et al.
Copending U.S. Appl. No. 13/758,080, filed Feb. 4, 2013, Mesfin Ejerssa Janka, et al.
Office Action dated Apr. 18, 2013 received in co-pending U.S. Appl. No. 13/228,797.
Office Action dated Apr. 18, 2013 received in co-pending U.S. Appl. No. 13/228,813.
Office Action dated Apr. 29, 2013 received in co-pending U.S. Appl. No. 13/228,799.
Office Action dated May 31, 2013 received in co-pending U.S. Appl. No. 13/228,803.
Office Action dated Jun. 6, 2013 received in co-pending U.S. Appl. No. 13/228,809.
Office Action dated Jun. 6, 2013 received in co-pending U.S. Appl. No. 13/228,816.
PCT International Search Report and Written Opinion dated Jul. 29, 2013 for International Application No. PCT/US2013/044935.
PCT International Search Report and Written Opinion dated Aug. 9, 2013 for International Application No. PCT/US2013/044932.

(56) References Cited

OTHER PUBLICATIONS

Office Action dated Sep. 30, 2013 received in co-pending U.S. Appl. No. 13/758,070.
Office Action dated Sep. 30, 2013 received in co-pending U.S. Appl. No. 13/758,080.
Moldenhauer, et al., "Beitrage zur Furanchemie I", Justus Liebigs Annalen Der Chemie, vol. 580, 1953, pp. 169-190.
Office Action dated Oct. 25, 2013 received in co-pending U.S. Appl. No. 13/288,813.
PCT International Search Report and Written Opinion dated Oct. 31, 2013 for International Application No. PCT/US2013/050799.
Office Action dated Nov. 5, 2013 received in co-pending U.S. Appl. No. 13/228,797.
Office Action dated Nov. 8, 2013 received in co-pending U.S. Appl. No. 13/228,803.
Office Action dated Nov. 8, 2013 received in co-pending U.S. Appl. No. 13/758,070.
Office Action dated Nov. 12, 2013 received in co-pending U.S. Appl. No. 13/228,799.
Office Action dated Nov. 14, 2013 received in co-pending U.S. Appl. No. 13/228,809.
Office Action dated Nov. 18, 2013 received in co-pending U.S. Appl. No. 13/758,088.
Copending U.S. Appl. No. 14/084,165, filed Nov. 19, 2013, Ashfaq Shaikh et al.
PCT International Search Report and Written Opinion dated Nov. 28, 2013 for International Application No. PCT/US2013/050794.
Office Action dated Dec. 13, 2013 received in co-pending U.S. Appl. No. 13/228,816.
Office Action dated Dec. 16, 2013 received in co-pending U.S. Appl. No. 13/553,976.
Notice of Allowance dated May 13, 2014 received in co-pending U.S. Appl. No. 13/758,088.
PCT International Search Report and Written Opinion dated Jul. 27, 2012 for International Application No. PCT/US2012/037206.
PCT International Search Report and Written Opinion dated Dec. 30, 2013 for International Application No. PCT/US2013/056362.
Office Action dated Sep. 26, 2014, received in co-pending U.S. Appl. No. 13/758,072.
Notice of Allowance dated Dec. 17, 2014 received in co-pending U.S. Appl. No. 13/758,080.

* cited by examiner

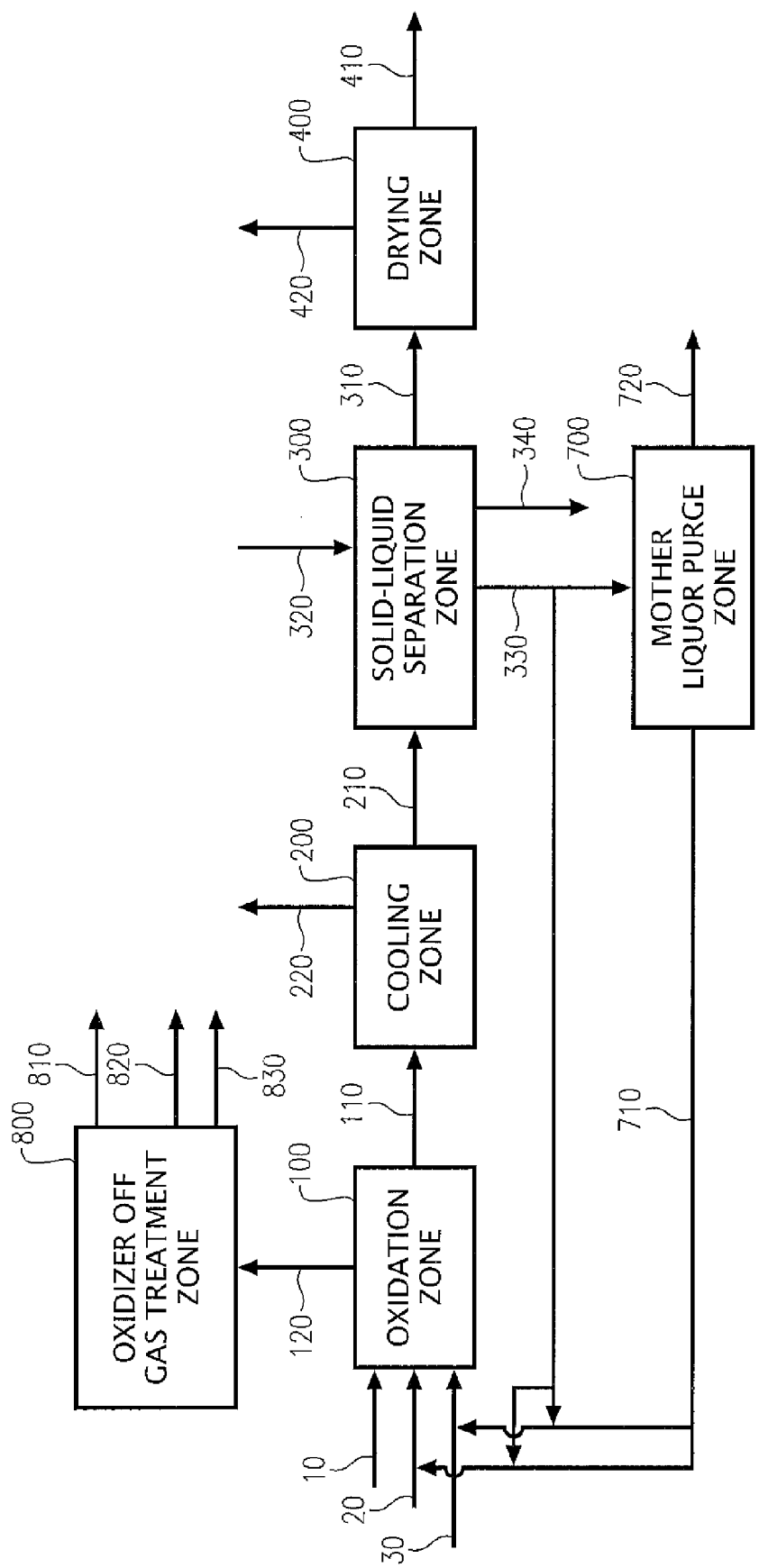

OXIDATION PROCESS TO PRODUCE A CRUDE DRY CARBOXYLIC ACID PRODUCT

CROSS-REFERENCE TO RELATED APPLICATIONS

This application is a continuation of U.S. Non-Provision application Ser. No. 13/758,088, filed on 4 Feb. 2013, which claims priority to U.S. Provisional Patent Application No. 61/694,982, filed on 30 Aug. 2012, the entire disclosure of which is incorporated herein by reference.

FIELD OF THE INVENTION

The present invention relates to a process to produce a carboxylic acid composition. The process comprises oxidizing at least one oxidizable compound in an oxidizable raw material stream in the presence of an oxidizing gas stream, solvent stream, and at least one catalyst system. More particularly, the process comprises oxidizing at least one oxidizable compound selected from the following group: 5-(hydroxymethyl)furfural (5-HMF), 5-HMF esters (5-R (CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feed-stocks of 5-HMF and 5-HMF esters and mixed feed-stocks of 5-HMF and 5-HMF ethers and mixed feed-stocks of 5-HMF and 5-alkyl furfurals in the presence of oxygen, a saturated organic acid solvent having from 2-6 carbon atoms, and a catalyst system at a temperature of about 100° C. to about 220° C. to produce the carboxylic acid composition comprising furan-2,5-dicarboxylic acid to generate a crude carboxylic acid slurry comprising FDCA, cooling a crude carboxylic acid slurry in cooling zone to form a cooled slurry stream. The cooled slurry stream is routed to a solid-liquid separation zone to generate a crude wet cake stream comprising FDCA that is dried in a drying zone to generate a dry carboxylic acid product stream comprising crude FDCA (cFDCA).

BACKGROUND OF THE INVENTION

Aromatic dicarboxylic acids, such as terephthalic acid and isophthalic acid, are used to produce a variety of polyester products. Important examples of which are poly(ethylene terephthalate) and its copolymers. These aromatic dicarboxylic acids are synthesized by the catalytic oxidation of the corresponding dialkyl aromatic compounds which are obtained from fossil fuels, which is disclosed in U.S. Patent Application 2006/0205977 A1), which is herein incorporated by reference to the extent it does not contradict the statements herein.

There is a growing interest in the use of renewable resources as feed stocks for the chemical industry mainly due to the progressive reduction of fossil reserves and their related environmental impacts. Furan-2,5-dicarboxylic acid (FDCA) is a versatile intermediate considered as a promising closest biobased alternative to terephthalic acid and isophthalic acid. Like aromatic diacids, FDCA can be condensed with diols such as ethylene glycol to make polyester resins similar to polyethylene terephthalate (PET) (Gandini, A.; Silvestre, A. J; Neto, C. P.; Sousa, A. F.; Gomes, M. *J. Poly. Sci. A* 2009, 47, 295.). FDCA has been prepared by oxidation of 5-(hydroxymethyl) furfural (5-HMF) under air using homogenous catalysts as disclosed in US2003/0055271 A1 and in Partenheimer, W.; Grushin, V. V. *Adv. Synth. Catal.* 2001, 343, 102-111. However, achieving high yields has proved difficult.

A maximum of 44.8% yield using Co/Mn/Br catalysts system and a maximum of 60.9% yield was reported using Co/Mn/Br/Zr catalysts combination.

Therefore, there is a need in the chemical industry for an inexpensive and high yield process to make a crude FDCA.

BRIEF DESCRIPTION OF THE DRAWINGS

FIG. 1 illustrates different embodiments of the invention wherein a process to produce a crude purified carboxylic acid 410 is provided.

DETAILED DESCRIPTION

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+/−37° F.), an intermediate numerical range of 43° F. to 81° F. (62° F.+/−19° F.), and a narrow numerical range of 53° F. to 71° F. (62° F.+/−9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively In one embodiment of the invention, a process is provided to produce a dry crude carboxylic acid 410 comprising furan-2,5-dicarboxylic acid (FDCA). Embodiments of the process are represented in FIG. 1. The process comprises oxidizing at least one oxidizable compound in an oxidizable raw material stream 30 in the presence of an oxidizing gas stream 10, solvent stream 20, and at least one catalyst system. The oxidizable raw material stream 30 comprises at least one oxidizable compound suitable to produce a carboxylic acid composition 110 comprising FDCA. The amount of FDCA in the carboxylic acid composition 110 can range from greater than 10 by weight percent in the carboxylic acid composition 110, greater than 20 by weight percent in the carboxylic acid composition 110, greater than 30 by weight percent in the carboxylic acid composition 110. The carboxylic acid composition 110 comprises FDCA and solvent.

In another embodiment of the invention, the process comprises oxidizing at least one oxidizable compound in an oxidizable raw material stream 30 in the presence of an oxidizing gas stream 10, solvent stream 20, and at least one catalyst system. The oxidizable raw material stream 30 comprises at least one oxidizable compound selected from the group consisting of 5-(hydroxymethyl)furfural (5-HMF), 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feedstocks of 5-HMF and 5-HMF esters, mixed feedstocks of 5-HMF and 5-HMF ethers, mixed feedstocks of 5-HMF and 5-alkyl furfurals to generate a carboxylic acid composition comprising FDCA. The process includes cooling the carboxylic acid composition 110 in a cooling zone 200. The cooled slurry stream 210 is routed to a solid-liquid separation zone 300 to generate a wet cake stream 310 comprising FDCA that is dried in a drying zone 400 to generate a dried, crude carboxylic acid 410 comprising purified FDCA.

In one embodiment of the invention, a process is provided to produce a dried, crude carboxylic acid 410 comprising dried, furan-2,5-dicarboxylic acid (FDCA) and comprises the following steps:

Step (a) comprises oxidizing at least one oxidizable compound in an oxidizable raw material stream 30 in the presence of an oxidizing gas stream 10, solvent stream 20, and at least one catalyst system in a primary oxidation zone 100 which comprises at least one primary oxidizer reactor to produce a carboxylic acid composition 110 comprising furan-2,5-dicarboxylic (FDCA); wherein the oxidizable raw material stream 30 comprises at least one oxidizable compound selected from the group consisting of 5-(hydroxymethyl)furfural (5-HMF), 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feedstocks of 5-HMF and 5-HMF esters, mixed feedstocks of 5-HMF and 5-HMF ethers, and mixed feedstocks of 5-HMF and 5-alkyl furfurals. Structures for the various oxidizable raw material compounds are outlined below:

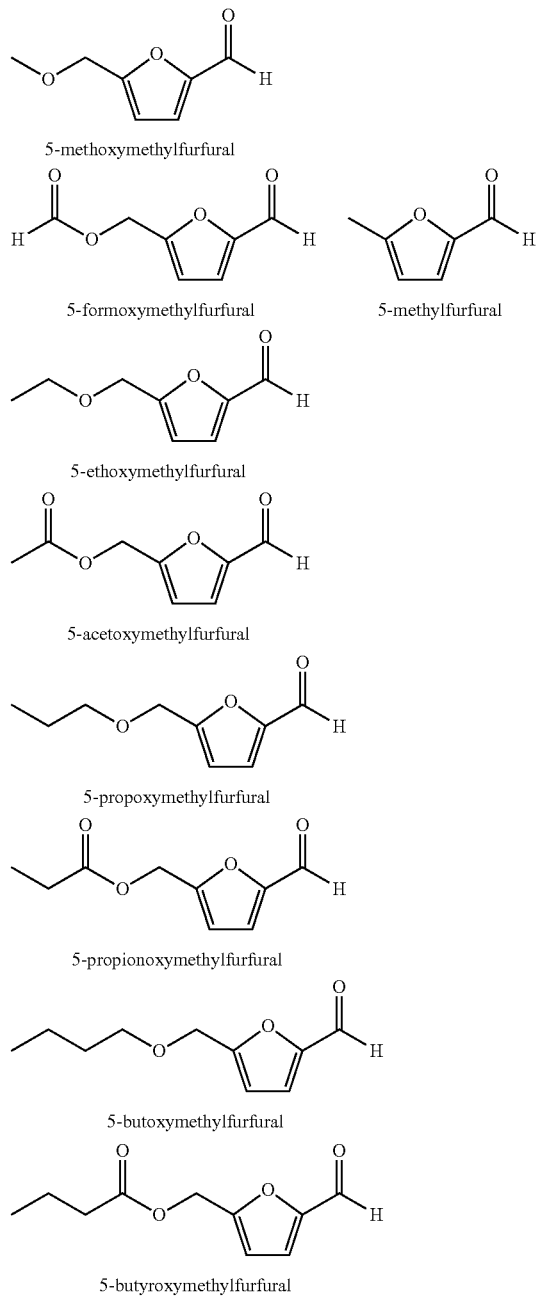

Preferred 5-HMF Derivative Feeds 5-methoxymethylfurfural 5-formoxymethylfurfural 5-methylfurfural 5-ethoxymethylfurfural 5-acetoxymethylfurfural 5-propoxymethylfurfural 5-propionoxymethylfurfural 5-butoxymethylfurfural 5-butyroxymethylfurfural 5-HMF feed is oxidized with elemental O2 in a multi-step reaction to form FDCA with 5-formyl furan-2-carboxylic acid (FFCA) as a key intermediate eq 1. Oxidation of 5-(acetoxymethyl)furfural (5-AMF), which contains an oxidizable ester and aldehydes moieties, produces FDCA, FFCA, and acetic acid, eq 2. Similarly oxidation of 5-(ethoxymethyl) furfural (5-EMF) produces FDCA, FFCA, 5-(ethoxycarbonyl)furan-2-carboxylic acid (EFCA) and acetic acid, eq 3.

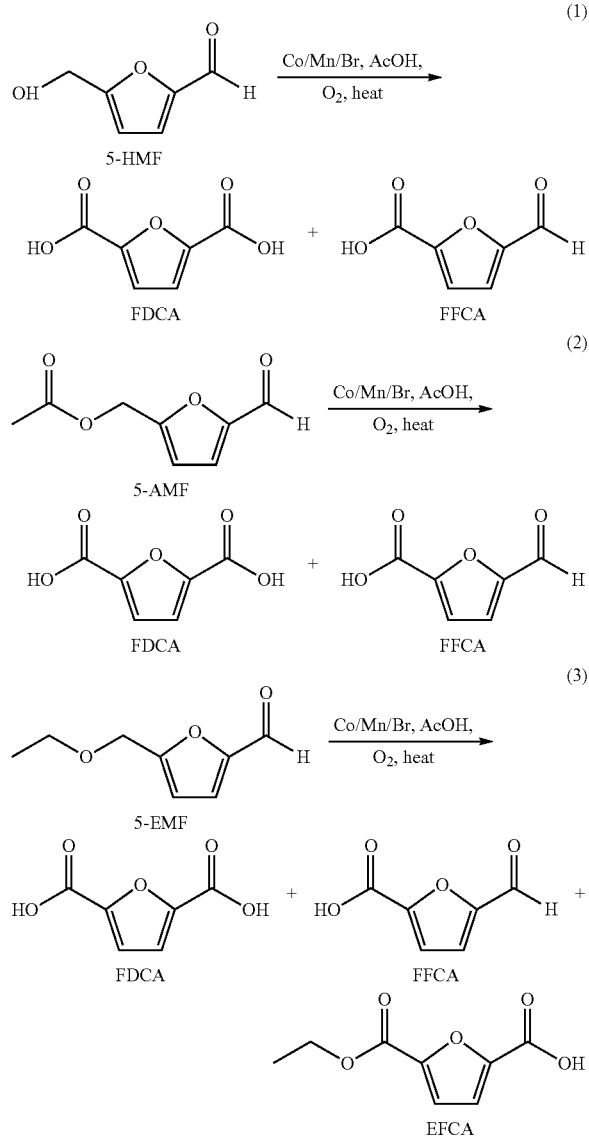

In one embodiment of this invention, streams routed to the primary oxidation zone 100 comprises an oxidizing gas stream 10 comprising oxygen and a solvent stream 20 comprising solvent, an oxidizable raw material stream 30, and a catalyst system. Oxidizable raw material stream 30 comprises a continuous liquid phase. In another embodiment of the invention, the oxidizable raw material stream 30, the oxidizing gas stream 10, the solvent stream 20 and the catalyst system can be fed to the primary oxidization zone 100 as separate and individual streams or combined in any combination prior to entering the primary oxidation zone 100 wherein said feed streams may enter at a single location or in multiple locations in the primary oxidization zone 100.

The carboxylic acid composition 110 comprises FDCA and FFCA. In another embodiment the FFCA in the carboxylic acid composition 110 ranges from about 0.1 wt % (weight percent) to about 4 wt % or 0.1 wt % to about 0.5 wt %, or 0.1 wt % to about 1 wt %. In another embodiment of the invention the carboxylic acid composition 110 comprises FDCA and FFCA and at least one of 2,5-diformylfuran in an amount ranging from 0 wt % to about 0.2 wt %, levulinic acid in an amount ranging from 0 wt % to 0.5 wt %, succinic acid in an amount ranging from 0 wt % to 0.5 wt % and acetoxy acetic acid in an amount ranging from 0 wt % to 0.5 wt %.

In another embodiment of the invention the carboxylic acid composition 110 comprises FDCA, FFCA and EFCA. In other embodiment of the invention the EFCA in the carboxylic acid composition 110 in an range from about 0.05 wt % to 4 wt %, or about 1 wt % to 2 wt %.

The catalyst system comprises at least one catalyst suitable for oxidation. Any catalyst known in the art capable of oxidizing the oxidizable compound can be utilized. Example of suitable catalysts comprise at least one selected from, but are not limited to, cobalt, bromine and manganese compounds, which are soluble in the selected oxidation solvent. In another embodiment of the invention, the catalyst system comprises cobalt, manganese and bromine wherein the weight ratio of cobalt to manganese in the reaction mixture is from about 10 to about 400 and the weight ratio of cobalt to bromine is from about 0.7 to about 3.5.

The oxidizing gas stream comprises oxygen. Examples include, but are not limited to, air and purified oxygen. The amount of oxygen in the primary oxidation zone ranges from about 5 mole % to 45 mole %, 5 mole to 60 mole % 5 mole % to 80 mole %.

Suitable solvents include water and the aliphatic solvents. In an embodiment of the invention, the solvents are aliphatic carboxylic acids which include, but are not limited to, aqueous solutions of $C_2$ to $C_6$ monocarboxylic acids, e.g., acetic acid, propionic acid, n-butyric acid, isobutyric acid, n-valeric acid, trimethylacetic acid, caprioic acid, and mixtures thereof. In another embodiment of the invention, the solvent is volatile under the oxidation reaction conditions to allow it to be taken as an off-gas from the oxidation reactor. In yet another embodiment of the invention the solvent selected is also one in which the catalyst composition is soluble under the reaction conditions.

The most common solvent used for the oxidation is an aqueous acetic acid solution, typically having a concentration of 80 to 99 wt. %. In especially preferred embodiments, the solvent comprises a mixture of water and acetic acid which has a water content of 0% to about 15% by weight. Additionally, a portion of the solvent feed to the primary oxidation reactor may be obtained from a recycle stream obtained by displacing about 80 to 90% of the mother liquor taken from the crude reaction mixture stream discharged from the primary oxidation reactor with fresh, wet acetic acid containing about 0 to 15% water.

Suitable solvents include, but are not limited to, aliphatic mono-carboxylic acids, preferably containing 2 to 6 carbon atoms and mixtures thereof and mixtures of these compounds with water. Examples of aliphatic mono-carboxylic acids, include, but are not limited to acetic acid.

Generally, the oxidation temperature can vary from about 100° C. to about 220° C. and from about 110° C. to about 160° C.

In another embodiment of the invention, a process is provided to produce furan-2,5-dicarboxylic acid (FDCA) in high yields by liquid phase oxidation that minimizes solvent and starting material loss through carbon burn. The process comprises oxidizing at least one oxidizable compound in an oxidizable raw material stream 30 in the presence of an oxidizing gas stream 10, solvent stream 20, and at least one catalyst system in a primary oxidation zone 100; wherein the oxidizable compound is at least one selected from the group consisting of H(C=O)—R—(C=O)H, HOH2C—R—(C=O) H, and 5-(hydroxymethyl)furfural (5-HMF). The oxidizable compound can be oxidized in a solvent comprising acetic acid with or without the presence of water with oxygen in the presence of a catalyst system comprising cobalt, manganese and bromine, wherein the weight ratio of cobalt to manganese in the reaction mixture is from about 10 to about 400 and the weight ratio of cobalt to bromine is from about 0.7 to about 3.5. Such a catalyst system with improved Co:Mn ratio can lead to high yield of FDCA. In this process, the oxidation temperature can vary from about 100° C. to about 220° C., or another range from about 110° C. to about 160° C., which can minimize carbon burn. The cobalt concentration of the catalyst can range from about 1000 ppm to about 6000 ppm, and the amount of manganese from about 2 ppm to about 600 ppm, and the amount of bromine from about 300 ppm to about 4500 ppm with respect to the total weight of the liquid in the reaction medium of the primary oxidation zone 100. As used herein, process temperature is the temperature of the reaction mixture within the primary oxidation zone where liquid is present as the continuous phase. The primary oxidizer reactor will typically be characterized by a lower section where gas bubbles are dispersed in a continuous liquid phase. Solids can also be present in the lower section. In the upper section of the primary oxidizer, gas is in the continuous phase and entrained liquid drops can also be present.

In various embodiments of the invention, the catalyst compositions employed in the processes of the invention comprise cobalt atoms, manganese atoms, and bromine atoms, supplied by any suitable means, as further described below. The catalyst composition is typically soluble in the solvent under reaction conditions, or it is soluble in the reactants fed to the oxidation zone. Preferably, the catalyst composition is soluble in the solvent at 40° C. and 1 atm, and is soluble in the solvent under the reaction conditions.

The cobalt atoms may be provided in ionic form as inorganic cobalt salts, such as cobalt bromide, cobalt nitrate, or cobalt chloride, or organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate.

The oxidation state of cobalt when added as a compound to the reaction mixture is not limited, and includes both the +2 and +3 oxidation states.

The manganese atoms may be provided as one or more inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrobromic acid, sodium bromide, ammonium bromide, potassium bromide, and tetrabromoethane. Hydrobromic acid, or sodium bromide may be preferred bromine sources.

In another embodiment of the invention, a process is provided for producing furan-2,5-dicarboxylic acid (FDCA) in high yields by liquid phase oxidation that minimizes solvent and starting material loss through carbon burn. The process comprises oxidizing at least one oxidizable compound in an oxidizable raw material stream 30 in the presence of an oxidizing gas stream 10, solvent stream 20, and at least one catalyst system in a primary oxidation zone 100; wherein the oxidizable compound is selected from the group consisting of 5-(acetoxymethyl)furfural (5-AMF), 5-(ethoxymethyl)furfural (5-EMF), 5-methyl furfural (5-MF); wherein the solvent stream 20 comprises acetic acid with or without the presence of water; wherein the catalyst system comprising cobalt, manganese and bromine, wherein the weight ratio of cobalt to manganese in the reaction mixture ranges from about 10 to about 400 and the weight ratio of cobalt to bromine is from about 0.7 to about 3.5. The catalyst system with improved Co:Mn ratio can lead to high yield of FDCA. In this process, the oxidation temperature can vary from about 100° C. to about 220° C., or from about 110° C. to about 160° C. to minimize carbon burn. The cobalt concentration in the catalyst system can range from about 500 ppm to about 6000 ppm, and the amount of manganese from about 2 ppm to about 600 ppm and the amount of bromine from about 300 ppm to about 4500 ppm with respect to the total weight of the liquid in the reaction medium. Mixed feedstocks of 5-AMF and 5-HMF or 5-EMF and 5-HMF or 5-MF and 5-HMF or 5-AMF, 5-EMF and 5-HMF, with varying ratios of the components can be used and similar results can be obtained.

In another embodiment of the invention, a process is provided for producing furan-2,5-dicarboxylic acid (FDCA) in high yields by liquid phase oxidation that minimizes solvent and starting material loss through carbon burn. The process comprises oxidizing at least one oxidizable compound in an oxidizable raw material stream 30 in the presence of an oxidizing gas stream 10, solvent stream 20, and at least one catalyst system in a primary oxidation zone 100; wherein said oxidizable compound is 5-(hydroxymethyl)furfural (5-HMF); wherein said solvent stream comprises acetic acid with or without the presence of water; wherein said catalyst system comprising cobalt, manganese and bromine, wherein the weight ratio of cobalt to manganese in the reaction mixture is from about 10 to about 400. In this process, the temperature can vary from about 100° C. to about 220° C., from about 105° C. to about 180° C., and from about 110° C. to about 160° C. The cobalt concentration of the catalyst system can range from about 1000 ppm to about 6000 ppm, and the amount of manganese can range from about 2 ppm to about 600 ppm, and the amount of bromine can range from about 300 ppm to about 4500 ppm with respect to the total weight of the liquid in the reaction medium.

In another embodiment of the invention, the process comprises oxidizing at least one oxidizable compound in an oxidizable raw material stream 30 in the presence of an oxidizing gas stream 10, solvent stream 20, and at least one catalyst system in a primary oxidation zone 100; wherein said oxidizable compound is 5-(hydroxymethyl)furfural (5-HMF); wherein said solvent stream comprises a saturated organic acid having from 2-6 carbon atoms with or without the presence of water at a temperature of 100° C. to 220° C. to produce a dicarboxylic acid composition; wherein the primary oxidation zone 100 comprises at least one primary oxidation reactor and wherein the catalyst system comprises cobalt in a range from about 500 ppm by weight to about 6000 ppm by weight with respect to the weight of the liquid in the reaction medium, manganese in an amount ranging from about 2 ppm by weight to about 600 ppm by weight with respect to the weight of the liquid in the reaction medium and bromine in an amount ranging from about 300 ppm by weight to about 4500 ppm by weight with respect to the weight of the liquid in the reaction medium.

In another embodiment of the invention, when the oxidizable raw material stream 30 comprises 5-HMF, then the cobalt to manganese ratio by weight is at least 10:1, 15:1, 20:1, 25:1, 30:1, 40:1, 50:1, 60:1, or 400 to 1.

In another embodiment of the invention, when the oxidizable material stream 30 comprises at least one oxidizable compound selected from the group consisting of 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R''-furfural, where R''=alkyl, cycloalkyl and aryl), mixed feedstocks of 5-HMF and 5-HMF esters, mixed feedstocks of 5-HMF and 5-HMF ethers, and mixed feed-stocks of 5-HMF and 5-alkyl furfurals, the cobalt to manganese ratio by weight of the catalyst system is at least 1:1, 10:1, 20:1, 50:1, 100:1, or 400:1.

In another embodiment of this invention, furan-2,5-dicarboxylic acid (FDCA) can be obtained by liquid phase oxidation of 5-(hydroxymethyl)furfural (5-HMF), 5-(acetoxymethyl)furfural (5-AMF) and 5-(ethoxymethyl)furfural (5-EMF) with molecular oxygen using Co/Mn/Br catalyst system in acetic acid solvent. After the oxidation of 5-HMF/5-AMF/5-EMF in presence of acetic acid, the FDCA precipitates out of solution. After filtration, washing with acetic acid and then with water, and drying, solids were obtained with a minimum of 90%, 92%, 94%, 96% FDCA content by weight.

In another embodiment of the invention, FDCA is obtained by liquid phase oxidation of 5-HMF, 5-AMF and 5-EMF with molecular oxygen using Co/Mn/Br catalyst system in acetic acid solvent. After the oxidation of 5-HMF/5-AMF/5-EMF in acetic acid, the FDCA precipitates out of solution. After filtration, washing with acetic acid and then with water, and drying, solids were obtained with a minimum of 96% FDCA content and a maximum b* of 15, 16, 17, 18, 19, or 20.

The b* is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow).

In another embodiment of the invention, a process is provided for producing furan-2,5-dicarboxylic acid (FDCA) in minimum yields of 80% or 85% or 90% or greater by liquid phase oxidation that minimizes solvent and starting material loss through carbon burn. As used herein, yield is defined as mass of FDCA obtained divided by the theoretical amount of FDCA that should be produced based on the amount of raw material use. For example, if one mole or 126.11 grams of 5-HMF are oxidized, it would theoretically generate one mole or 156.09 grams of FDCA. If for example, the actual amount of FDCA formed is only 150 grams, the yield for this reaction is calculated to be =(150/156.09) times 100, which equals a yield of 96%. The same calculation applies for oxidation reaction conducted using 5-HMF derivatives or mixed feeds.

In another embodiment of this invention, a process is provided comprising oxidizing at least one oxidizable compound in an oxidizable raw material stream 30 in the presence of an oxidizing gas stream 10, solvent stream 20, and at least one catalyst system in a primary oxidation zone 100; wherein said oxidizable compound is selected from the group consisting of H(C=O)—R—(C=O)H, HOH2C—R—(C=O)H, 5-(hydroxymethyl)furfural (5-HMF); wherein said solvent stream comprises acetic acid with or without the presence of water; wherein said catalyst system comprises cobalt, manganese and bromine, wherein the weight ratio of cobalt to manganese in the reaction mixture is from about 10 to about 400 and the weight ratio of cobalt to bromine is from about 0.7 to about 3.5. Such a catalyst system with improved Co:Mn and Co:Br ratio can lead to high yield of FDCA (minimum of 90%), decrease in the formation of impurities (measured by b*) causing color in the downstream polymerization process while keeping the amount of CO and CO$_2$ in the off-gas at a minimum.

The temperature in the primary oxidation zone can range from about 100° C. to about 220° C., and can range from about 110° C. to about 160° C. or can range from about 105° C. to about 180° C. or about 100° C. to about 200° C., or about 100° C. to about 190° C. One advantage of the disclosed primary oxidation conditions is low carbon burn as illustrated in Tables 1 to 3. Oxidizer off gas stream 120 is routed to the oxidizer off gas treatment zone 800 to generate an inert gas stream 810, liquid stream 820 comprising water, and a recovered oxidation solvent stream 830 comprising condensed solvent. In one embodiment, at least a portion of recovered oxidation solvent stream 830 is routed to wash solvent stream 320 to become a portion of the wash solvent stream 320 for the purpose of washing the solids present in the solid-liquid separation zone. In another embodiment, the inert gas stream 810 can be vented to the atmosphere. In yet another embodiment, at least a portion of the inert gas stream 810 can be used as an inert gas in the process for inerting vessels and or used for convey gas for solids in the process. In another embodiment, at least a portion of the energy in stream 120 is recovered in the form of stream and or electricity.

Step (b)

The crude carboxylic acid stream 110 comprising FDCA is routed to cooling zone 200 to generate a cooled crude carboxylic acid slurry stream 210 and a $1^{st}$ vapor stream 220 comprising oxidation solvent vapor. The cooling of crude carboxylic slurry stream 110 can be accomplished by any means known in the art; typically the cooling zone 200 comprises a flash tank. In another embodiment, a portion of up to 100% of the crude carboxylic acid slurry stream 110 is routed directly to solid-liquid separation zone 300, thus said portion is not subjected to cooling in cooling zone 200. The temperature of stream 210 can range from 35° C. to 160° C., 45° C. to 120° C., and preferably from 55° C. to 95° C.

Step (c) comprises isolating, washing, and dewatering solids present in the cooled crude carboxylic acid slurry stream 210 in the solid-liquid separation zone 300 to generate a crude carboxylic acid wet cake stream 310 comprising FDCA. These functions may be accomplished in a single solid-liquid separation device or multiple solid-liquid separation devices. The solid-liquid separation zone 300 comprises at least one solid-liquid separation device capable of separating solids and liquids, washing solids with a wash solvent stream 320, and reducing the % moisture in the washed solids to less than 30 weight %, less than 20 weight %, less than 15 weight %, and preferably less than 10 weight %.

Equipment suitable for the solid liquid separation zone 300 can typically be comprised of, but not limited to, the following types of devices: centrifuges, cyclones, rotary drum filters, belt filters, pressure leaf filters, candle filters, and the like. The preferred solid liquid separation device for the solid liquid separation zone 300 is a rotary pressure drum filter. The temperature of cooled crude carboxylic acid slurry stream 210 which is routed to the solid-liquid separation zone 300 can range from 50° C. to 140° C., 70° C. to 120° C., and is preferably from 75° C. to 95° C. Wash solvent stream 320 comprises a liquid suitable for displacing and washing oxidizer mother liquor from the solids.

In one embodiment of the invention, a suitable wash solvent comprises acetic acid. In another embodiment, a suitable wash solvent comprises acetic acid and water. In yet another embodiment, a suitable wash solvent comprises water up to 100% water. The temperature of the wash solvent can range from 20° C. to 135° C., 40° C. to 110° C., and preferably from 50° C. to 90° C. The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3.

After solids are washed in the solid liquid separation zone, they are dewatered. The term dewatering is defined as the reduction of solvent from the wet cake and does not require that the solvent be water or contain water. Dewatering involves reducing the mass of moisture present with the solids to less than 30% by weight, less than 25% by weight, less than 20% by weight, and most preferably less than 15% by weight resulting in the generation of a crude carboxylic acid wet cake stream 310 comprising FDCA. In one embodiment, dewatering is accomplished in a filter by passing a stream comprising gas through the solids to displace free liquid after the solids have been washed with a wash solvent. In an embodiment, dewatering of the wet cake solids in solid-liquid separation zone 300 can be implemented before washing and after washing the wet cake solids in zone 300 to minimize the amount of oxidizer solvent present in the wash liquor stream 340. In another embodiment, dewatering is achieved by centrifugal forces in a perforated bowl or solid bowl centrifuge.

Mother liquor stream 330 generated in solid-liquid separation zone 300 comprises oxidation solvent, catalyst, and impurities. From 5% to 95%, from 30% to 90%, and most preferably from 40 to 80% of mother liquor present in the crude carboxylic acid stream 110 is isolated in solid-liquid separation zone 300 to generate mother liquor stream 330 resulting in dissolved matter comprising impurities present mother liquor stream 330 not going forward in the process. In one embodiment, a portion of mother liquor stream 330 is routed to a purge zone a portion is at least 5 weight %, at least 25 weight %, at least 45 weight %, at least 55 weight % at least 75 weight %, at least 90 weight %. In another embodiment, at least a portion is routed back to the primary oxidation zone wherein a portion is at least 5 weight %. In yet another embodiment, at least a portion of mother liquor stream 330 is routed to a purge zone and to the primary oxidation zone wherein a portion is at least 5 weight %. In one embodiment, purge zone 700 comprises an evaporative step to separate oxidation solvent from stream 330 by evaporation.

Wash liquor stream 340 is generated in the solid-liquid separation zone 300 and comprises a portion of the mother liquor present in stream 210 and wash solvent wherein the ratio of mother liquor mass to wash solvent mass is less than 3 and preferably less than 2. In an embodiment, at least a portion of wash liquor stream 340 is routed to oxidation zone 100 wherein a portion is at least 5 weight %. In an embodiment, at least a portion of wash liquor stream is routed to purge zone 700 wherein a portion is at least 5 weight %. In another embodiment, at least a portion of wash liquor stream is routed to oxidation zone 100 and purge zone 700 wherein a portion is at least 5 weight %.

In another embodiment at least a portion of crude carboxylic acid slurry stream 110 up to 100 weight % is routed directly to solid-liquid separation zone 300, thus said portion will bypass the cooling zone 200.

In this embodiment, feed to solid-liquid separation zone 300 comprises at least a portion of crude carboxylic slurry stream 110 and wash solvent stream 320 to generate a crude carboxylic acid wet cake stream 310 comprising FDCA. Solids in the feed slurry are isolated, washed, and dewatered in solid-liquid separation zone 300. These functions may be accomplished in a single solid-liquid separation device or multiple solid-liquid separation devices. The solid-liquid separation zone comprises at least one solid-liquid separation device capable of separating solids and liquids, washing solids with a wash solvent stream 320, and reducing the % moisture in the washed solids to less than 30 weight %, less than 20 weight %, less than 15 weight %, and preferably less than 10 weight %. Equipment suitable for the solid liquid separation zone can typically be comprised of, but not limited to, the following types of devices: centrifuge, cyclone, rotary drum filter, belt filter, pressure leaf filter, candle filter, and the like. The preferred solid liquid separation device for the solid liquid separation zone is a continuous rotary pressure drum filter. The temperature of the crude carboxylic acid slurry feed stream which is routed to the solid-liquid separation zone 300 can range from 40° C. to 210° C., 60° C. to 170, ° C. and is preferably from 80° C. to 160° C. The wash stream 320 comprises a liquid suitable for displacing and washing mother liquor from the solids. In one embodiment, a suitable wash solvent comprises acetic acid and water. In another embodiment, a suitable wash solvent comprises water up to 100% water. The temperature of the wash solvent can range from 20° C. to 180° C., 40° C. and 150° C., and preferably from 50° C. to 130° C. The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3. After solids are washed in the solid liquid separation zone, they are dewatered. Dewatering involves reducing the mass of moisture present with the solids to less than 30% by weight, less than 25% by weight, less than 20% by weight, and most preferably less than 15% by weight resulting in the generation of a crude carboxylic acid wet cake stream 310. In one embodiment, dewatering is accomplished in a filter by passing a gas stream through the solids to displace free liquid after the solids have been washed with a wash solvent. In another embodiment, dewater of the wet cake in solid-liquid separation zone 300 can be implemented before washing and after washing the solids in zone 300 to minimize the amount of oxidizer solvent present in the wash liquor stream 340 by any method known in the art. In yet another embodiment, dewatering is achieved by centrifugal forces in a perforated bowl or solid bowl centrifuge.

Mother liquor stream 330 generated in solid-liquid separation zone 300 comprising oxidation solvent, catalyst, and impurities. From 5% to 95%, from 30% to 90%, and most preferably from 40 to 80% of mother liquor present in the crude carboxylic acid stream 110 is isolated in solid-liquid separation zone 300 to generate mother liquor stream 330 resulting in dissolved matter comprising impurities present mother liquor stream 330 not going forward in the process. In one embodiment, a portion of mother liquor stream 330 is routed to a purge zone a portion is at least 5 weight %, at least 25 weight %, at least 45 weight %, at least 55 weight % at least 75 weight %, at least 90 weight %. In another embodiment, at least a portion is routed back to the primary oxidation zone wherein a portion is at least 5 weight %. In yet another embodiment, at least a portion of mother liquor stream 330 is routed to a purge zone and to the primary oxidation zone wherein a portion is at least 5 weight %. In one embodiment, purge zone 700 comprises an evaporative step to separate oxidation solvent from stream 330 by evaporation.

Wash liquor stream 340 is generated in the solid-liquid separation zone 300 and comprises a portion of the mother liquor present in stream 210 and wash solvent wherein the ratio of mother liquor mass to wash solvent mass is less than 3 and preferably less than 2. In an embodiment, at least a portion of wash liquor stream 340 is routed to oxidation zone 100 wherein a portion is at least 5 weight %. In an embodiment, at least a portion of wash liquor stream is routed to purge zone 700 wherein a portion is at least 5 weight %. In another embodiment, at least a portion of wash liquor stream is routed to oxidation zone 100 and purge zone 700 wherein a portion is at least 5 weight %.

Step (d) Oxidizer mother liquor stream 330 comprises oxidation solvent, catalyst, soluble intermediates, and soluble impurities. It is desirable to recycle directly or indirectly at least a portion of the catalyst and oxidation solvent present in mother liquor stream 330 back to oxidation zone 100 wherein a portion is at least 5% by weight, at least 25%, at least 45%, at least 65%, at least 85%, at least 95%. Direct recycling at least a portion of the catalyst and oxidation solvent present in mother liquor stream 330 comprises directly routing a portion of stream 330 to oxidizer zone 100. Indirect recycling at least a portion of the catalyst and oxidation solvent present in mother liquor stream 330 to oxidation zone 100 comprises routing at least a portion of stream 330 to at least one intermediate zone wherein stream 330 is treated to generate a stream or multiple streams comprising oxidation solvent and or catalyst that are routed directly to oxidation zone 100. A purge zone can be utilized to separate components of stream 330 for recycle to the process while also isolating those components not to be recycled but rather removed from the process as a purge stream.

Impurities in stream 330 can originate from one or multiple sources. Impurities in stream 330 comprise impurities introduced into the process by feeding streams to oxidation zone 100 that comprise impurities. An impurity is defined as any molecule not required for the proper operation of oxidation zone 100. For example, oxidation solvent, a catalyst system, a gas comprising oxygen, and oxidizable raw material comprising at least one compound selected from the group of formula: 5-(hydroxymethyl)furfural (5-HMF), 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feed-stocks of 5-HMF and 5-HMF esters and mixed feed-stocks of 5-HMF and 5-HMF ethers and mixed feed-stocks of 5-HMF and 5-alkyl furfurals comprise molecules are required for the proper operation of oxidation zone 100 and are not considered impurities. Also, chemical intermediates formed in oxidation zone 100 that lead to or contribute to chemical reactions that lead to desired products are not considered impurities. Oxidation by-products that do not lead to desired product are defined as impurities. Impurities may enter oxidation zone 100 through recycle streams routed to oxidation zone 100 or by impure raw material streams fed to oxidation zone 100.

In one embodiment, it is desirable to isolate a portion of the impurities from mother liquor stream 330 and purge or remove them from the process as purge stream 720. From 5% to 100% by weight, of mother liquor stream 330 generated in solid-liquid separation zone 300 is routed to purge zone 700 wherein a portion of the impurities present in stream 330 are isolated and exit the process as purge stream 720, wherein a portion is 5% by weight or greater, 25% by weight or greater, 45% by weight or greater, 65% by weight or greater, 85% by weight or greater, 95% by weight or greater. Recovered solvent stream 710 comprises oxidation solvent and catalyst isolated from stream 330 and is recycled to the process. In one embodiment, recovered solvent stream 710 is recycled to oxidation zone 100 and contains greater than 30%, greater than 50%, greater than 80%, or greater than 90% of the catalyst that entered the mother liquor purge zone 700 in stream 330. In another embodiment, at least a portion of mother liquor stream 330 is routed directly to oxidation zone 100 without first being treated in purge zone 700. In one embodiment, purge zone 700 comprises an evaporative step to separate oxidation solvent from stream 330 by evaporation.

Step (e) comprises drying crude carboxylic acid wet cake stream 310 in a dryer zone to generate a dry crude carboxylic acid stream 410 comprising FDCA and a 2nd vapor stream 420 comprising wash solvent. In one embodiment, vapor stream 420 comprises wash solvent vapor. In another embodiment, vapor stream 420 comprises oxidation solvent and wash solvent. The drying zone comprises at least one dryer and can be accomplished by any means known in the art that is capable of evaporating at least 10% of the volatiles remaining in the low impurity wet cake stream 310 to produce the dry crude carboxylic acid stream 410 comprising FDCA and a vapor stream 420. For example, indirect contact dryers including a rotary stream tube dryer, a Single Shaft Porcupine RTM dryer, and a Bepex Solidaire RTM dryer. Direct contact dryers including a fluid bed dryer, a ring dryer, and drying in a convey line can be used for drying to produce stream 410. The dried crude carboxylic acid stream 410 comprising FDCA can be a carboxylic acid composition with less than 8% moisture, preferably less than 5% moisture, and more preferably less than 1% moisture, and even more preferably less than 0.5%, and yet more preferably less than 0.1%.

In one embodiment, a vacuum system can be utilized to pull vapor stream 420 from drying zone 400. If a vacuum system is used in this fashion, the pressure of stream 420 at the dryer outlet can range from about 760 mmHg absolute to about 400 mmHg absolute, from about 760 mmHg absolute to about 600 mmHg absolute, from about 760 mmHg absolute to about 700 mmHg absolute, from about 760 mmHg absolute to about 720 mmHg absolute, from about 760 mmHg absolute to about 740 mmHg absolute, wherein pressure is measured in mmHg above absolute vacuum. The contents of the conduit between solid-liquid separation zone 300 and drying zone 400 utilized to transfer wet cake stream 410 comprises wet cake stream 410 and gas wherein gas is the continuous phase. In one embodiment, the difference in pressure where wet cake stream 410 exits solid liquid separation zone 300 and where vapor stream 420 exits drying zone 400 is less than 2 psi, less than 0.8 psi, and preferably less than 0.4 psi. In one embodiment, a rotary air-lock valve is used to discharge solids from the dryer zone to a location outside the dryer zone that has a higher pressure than the drying zone. In this embodiment, the rotary air-lock valve serves to meter dry solids from the dryer into a higher pressure environment.

In an embodiment of the invention, the dried crude carboxylic acid stream 410 has a b* less than about 20.0. In another embodiment of the invention, the b* color of the dried carboxylic acid stream 410 is less than about 9.0. In another embodiment of the invention, the b* color of the dried carboxylic acid stream 410 is less than about 5.0. The b* color is one of the three-color attributes measured on a spectroscopic reflectance-based instrument. A Hunter Ultrascan XE instrument in reflectance mode is typically the measuring device. Positive readings signify the degree of yellow (or absorbance of blue), while negative readings signify the degree of blue (or absorbance of yellow).

One function of drying zone 400 is to remove by evaporation oxidation solvent comprising a mono-carboxylic acid with 2 to 6 carbons that can be present in the crude carboxylic acid wet cake stream 310. The % moisture in crude carboxylic acid wet cake stream 310 typically ranges from 4.0% by weight to 30% by weight depending on the operation conditions of the solid-liquid separation zone 300. If for example, the liquid portion of stream 310 is about 90% acetic acid, the amount of acetic acid present in stream 310 can range from about 3.6 weight % to 27 weight %.

It should be appreciated that the process zones previously described can be utilized in any other logical order to produce the dried, purified carboxylic acid 710. It should also be appreciated that when the process zones are reordered that the process conditions may change. It is also understood that all percent values are weight percents.

Since numerous modifications and changes will readily occur to those skilled in the art, it is not desired to limit this invention to the exact process and operations illustrated and described above, and accordingly all suitable modifications and equivalents may be resorted to, falling within the scope of the invention

EXAMPLES

This invention can be further illustrated by the following examples of embodiments thereof, although it will be understood that these examples are included merely for the purposes of illustration and are not intended to limit the scope of the invention unless otherwise specifically indicated.

Air oxidation of 5-HMF/5-AMF/5-EMF using cobalt, manganese and ionic bromine catalysts system in acetic acid solvent were conducted. After reaction the heterogeneous mixture was filtered to isolate the crude FDCA. The crude FDCA was washed with acetic acid two times and then twice with DI water. The washed crude FDCA was oven dried at 110° C. under vacuum overnight. The solid and the filtrate were analyzed by Gas Chromatography using BSTFA derivatization method. b* of the solid was measured using a Hunter Ultrascan XE instrument. The Off-gas was analyzed for CO and $CO_2$ by ND-1R (ABB, Advanced Optima) and $O_2$ by a paramagnetism detection system (Servomex, 1440 Model).

As shown in Tables 1 to 3 we have discovered conditions that to generate yields of FDCA up to 89.4%, b*<6, and low carbon burn (<0.00072 mol/min $CO+CO_2$)

TABLE 1

Results from semi-batch reactions using 5-HMF feed.*

| Example | Bromide source | Co conc (ppm) | Mn conc (ppm) | Br conc (ppm) | yield of FDCA (%) | yield of FFCA (%) | CO (total mol) | $CO_2$ (total mol) | $CO_x$ (mol/min) | color (b*) |
|---|---|---|---|---|---|---|---|---|---|---|
| 1a | solid NaBr | 2000 | 93.3 | 3000 | 81.6 | 0.81 | 0.013 | 0.078 | 0.000758 | 13.91 |
| 1b | solid NaBr | 2000 | 93.3 | 3000 | 82.6 | 0.87 | 0.013 | 0.092 | 0.000875 | 14.14 |
| 1c | aqueous HBr | 2000 | 93.3 | 3000 | 89.4 | 0.58 | 0.003 | 0.061 | 0.000533 | 5.85 |
| 1d | aqueous HBr | 2000 | 93.3 | 3000 | 88.6 | 0.8 | 0.0037 | 0.061 | 0.000539 | 6.18 |

*P = 130 psig, $CO_x$ (mol/min) = CO (mol/min) + CO2 (mol/min).

TABLE 2

Results from semi-batch reactions using 5-AMF feed.*

| Example | Co conc (ppmw) | Mn conc (ppmw) | Br conc (ppmw) | Temperature (° C.) | % yield of FDCA | % yield of FFCA | CO (total mol) | CO2 (total mol) | $CO_x$(mol/min) | color (b*) |
|---|---|---|---|---|---|---|---|---|---|---|
| 2a | 2500 | 116.8 | 2500 | 130 | 88.2 | 0.25 | 0.0052 | 0.08 | 0.00071 | 4.4 |
| 2b | 2000 | 93.5 | 3000 | 130 | 90.2 | 0.16 | 0.005 | 0.046 | 0.000425 | 6.8 |

*P = 130 psig, $CO_x$ (mol/min) = CO (mol/min) + CO2 (mol/min).

TABLE 3

Results from semi-batch reactions using 5-EMF feed.*

| Example | Co conc (ppmw) | Mn conc (ppmw) | Br conc (ppmw) | Temperature (° C.) | % yield of FDCA | % yield of FFCA | % yield of EFCA | CO (total mol) | CO2 (total mol) | $CO_x$ (mol/min) | color (b*) |
|---|---|---|---|---|---|---|---|---|---|---|---|
| 3a | 2500 | 116.8 | 2500 | 130 | 88.8 | 0.02 | 0.225 | 0.008 | 0.068 | 0.000633333 | 3.97 |
| 3b | 2000 | 93.5 | 3000 | 130 | 88.0 | 0.09 | 0.43 | 0.008 | 0.078 | 0.000716667 | 2.48 |
| 3c | 2000 | 93.5 | 3000 | 105 | 86.0 | 2.92 | 1.4 | 0.005 | 0.046 | 0.000425 | 6.66 |
| 3d | 2500 | 116.8 | 2500 | 130 | 87.4 | 0.42 | 1.3 | 0.009 | 0.064 | 0.000608333 | 2.74 |

*P = 130 psig, $CO_x$ (mol/min) = CO (mol/min) + CO2 (mol/min).

Analytical

Gas Chromatographic Method Process samples were analyzed using a Shimadzu gas chromatograph Model 2010 (or equivalent) equipped with a split/heated injector (300° C.) and a flame ionization detector (300° C.). A capillary column (60 meter×0.32 mm ID) coated with (6% cyanopropylphenyl)-methylpolysiloxane at 1.0 μm film thickness (such as DB-1301 or equivalent) was employed. Helium was used as the carrier gas with an initial column head pressure of 29.5 psi and an initial column flow of 3.93 mL/minute while the carrier gas linear velocity of 45 cm/second was maintained constant throughout the entire oven temperature program. The column temperature was programmed as follows: The initial oven temperature was set at 80° C. and was held for 6 minutes, the oven was ramped up to 150° C. at 4° C./minute and was held at 150° C. for 0 minute, the oven was ramped up to 240° C. at 10° C./minute and was held at 240° C. for 5 minutes, then the oven was ramped up to 290° C. at 10° C./minute and was held at 290° C. for 17.5 minutes (the total run time was 60 mins). 1.0-μl of the prepared sample solution was injected with a split ratio of 40:1. EZ-Chrom Elite chromatography data system software was used for data acquisition and data processing. The sample preparation was done by weighing 0.1 g (accurate to 0.1 mg) of sample in a GC vial and adding 200.0 μl ISTD solution (1% by volume of decane in pyridine) and 1000 μl of BSTFA (N,O-bis(trimethylsilyl)trifluoroacetamide) with 1% TMSCl (trimethylchlorosilane) to the GC vial. The content was heated at 80° C. for 30 minutes to ensure complete derivatization. 1.0-μl of this prepared sample solution was injected for GC analysis.

Color Measurement. 1) Assemble the Carver Press die as instructed in the directions—place the die on the base and place the bottom 40 mm cylinder polished side face-up.

2) Place a 40 mm plastic cup (Chemplex Plasticup, 39.7×6.4 mm) into the die.

3) Fill the cup with the sample to be analyzed. The exact amount of sample added is not important.

4) Place the top 40 mm cylinder polished side face-down on the sample.

5) Insert the plunger into the die. No "tilt" should be exhibited in the assembled die.

6) Place the die into the Carver Press, making sure that it is near the center of the lower platen. Close the safety door.

7) Raise the die until the upper platen makes contact with the plunger. Apply >20,000 lbs. pressure. Then allow the die to remain under pressure for approximately 3 minutes (exact time not critical).

8) Release the pressure and lower the lower platen holding the die.

9) Disassemble the die and remove the cup. Place the cup into a labeled plastic bag (Nasco Whirl-Pak 4 oz.).

10) Using a HunterLab Colorquest XE colorimeter, create the following method (Hunterlab EasyQuest QC software, version 3.6.2 or later) Mode: RSIN-LAV (Reflectance Specular Included-Large Area View)

Measurements:
CIE L* a* b*
CIEXYZ

11) Standardize the instrument as prompted by the software using the light trap accessory and the certified white tile accessory pressed against the reflectance port.

12) Run a green tile standard using the certified white tile and compare the CIE X, Y, and Z values obtained against the certified values of the tile. The values obtained should be ±0.15 units on each scale of the stated values.

13) Analyze the sample in the bag by pressing it against the reflectance port and obtaining the spectrum and L*, a*, b* values. Obtain duplicate readings and average the values for the report.

Claims Not Limited to Disclosed Embodiments

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

We claim:

1. A process to produce a carboxylic acid composition, said process comprising:
   (a) oxidizing in an primary oxidation zone an oxidizable compound in a oxidizable raw material stream in the presence of a solvent stream, an oxidizing gas stream, and a catalyst system to produce a carboxylic acid composition comprising furan-2,5-dicarboxylic acid (FDCA),
   wherein said oxidizable raw material stream comprises at least one compound selected from the group consisting of 5-(hydroxymethyl)furfural (5-HMF), 5-HMF esters (5-R(CO)OCH$_2$-furfural where R =alkyl, cycloalkyl, or aryl), 5-HMF ethers (5-R'OCH$_2$-furfural, where R'=alkyl, cycloalkyl, or aryl), 5-alkyl furfurals (5-R"-furfural, where R"=alkyl, cycloalkyl, or aryl), mixed feedstocks of 5-HMF and 5-HMF esters, mixed feedstocks of 5-HMF and 5-HMF ethers, and mixed feedstocks of 5-HMF and 5-alkyl furfurals, and
   wherein said catalyst system comprises cobalt, manganese, and bromine;
   (b) routing the carboxylic acid composition to a solid-liquid separation zone to generate a mother liquor stream and a wet carboxylic acid composition;
   (c) routing the wet carboxylic acid composition to a drying zone to produce a dried crude carboxylic acid composition.

2. A process according to claim 1 wherein a portion of said mother liquid stream is routed to a purge zone to generate a recovered solvent stream comprising solvent and catalyst.

3. A process according to claim 1 wherein said oxidizing is accomplished at a temperature of about 100° C. to about 220° C. to produce said carboxylic acid composition; wherein said primary oxidation zone comprises at least one oxidation reactor; and wherein the yield of furan-2,5-dicarboxylic acid (FDCA) is greater than 60%.

4. A process according to claim 1 wherein an offgas from said primary oxidation zone is routed to an oxidizer offgas treatment zone.

5. A process according to claim 1 wherein said oxidizable raw material stream comprises at least one compound selected from the group consisting of 5-(hydroxymethyl)furfural (5-HMF), 5-HMF esters (5-R(CO)OCH$_2$-furfural where R =alkyl, cycloalkyl, or aryl), 5-HMF ethers (5-R'OCH$_2$-furfural, where R'=alkyl, cycloalkyl, or aryl), and wherein the yield of furan-2,5-dicarboxylic acid is greater than 70%.

6. A process according to claim 1 wherein said oxidizable raw material stream comprises at least one selected from the group consisting of 5-(hydroxymethyl)furfural (5-HMF), 5-HMF esters (5-R(CO)OCH$_2$-furfural where R =alkyl, cycloalkyl, or aryl), 5-HMF ethers (5-R'OCH$_2$-furfural, where R'=alkyl, cycloalkyl, or aryl), and wherein the yield of furan-2,5-dicarboxylic acid is greater than 80%.

7. A process according to claim 1 wherein said oxidizable raw material stream comprises at least one selected from the group consisting of 5-(hydroxymethyl)furfural (5-HMF), 5-HMF esters (5-R(CO)OCH$_2$-furfural where R =alkyl, cycloalkyl, or aryl), 5-HMF ethers (5-R'OCH$_2$-furfural, where R'=alkyl, cycloalkyl, or aryl), and wherein the yield of furan-2,5-dicarboxylic acid is greater than 90%.

8. A process according to claim 1 wherein said oxidizable raw material stream comprises at least one selected from the group consisting of 5-(hydroxymethyl)furfural (5-HMF), 5-HMF esters (5-R(CO)OCH$_2$-furfural where R =alkyl, cycloalkyl, or aryl), 5-HMF ethers (5-R'OCH$_2$-furfural, where R'=alkyl, cycloalkyl, or aryl), and wherein the yield of furan-2,5-dicarboxylic acid is greater than 95%.

9. A process according to claim 8 wherein said catalyst system comprises cobalt in a range from about 500 ppm to about 6000 ppm with respect to the weight of the liquid in the primary oxidation zone, manganese in an amount ranging from about 2ppm to about 600 ppm by weight with respect to the weight of the liquid in the primary oxidation zone, and bromine in an amount ranging from about 300 ppm to about 4500 ppm by weight with respect to the weight of the liquid in the primary oxidation zone.

10. A process according to claim 8 wherein said catalyst system comprises cobalt in a range from about 700 ppm to about 4500 ppm with respect to the weight of the liquid in the primary oxidation zone, manganese in an amount ranging from about 20 ppm to about 400 ppm by weight with respect to the weight of the liquid in the primary oxidation zone, and bromine in an amount ranging from about 700 ppm to about 4000 ppm by weight with respect to the weight of the liquid in the primary oxidation zone.

\* \* \* \* \*